(12) United States Patent
Pilly et al.

(10) Patent No.: US 10,420,937 B2
(45) Date of Patent: Sep. 24, 2019

(54) METHOD AND APPARATUS TO DETERMINE OPTIMAL BRAIN STIMULATION TO INDUCE DESIRED BEHAVIOR

(71) Applicant: HRL Laboratories, LLC, Malibu, CA (US)

(72) Inventors: Praveen K. Pilly, West Hills, CA (US); Michael D. Howard, Westlake Village, CA (US); Heiko Hoffmann, Simi Valley, CA (US); Tsai-Ching Lu, Thousand Oaks, CA (US); Kang-Yu Ni, Calabasas, CA (US); David W. Payton, Calabasas, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 15/960,456

(22) Filed: Apr. 23, 2018

(65) Prior Publication Data
US 2018/0236230 A1     Aug. 23, 2018

Related U.S. Application Data

(63) Continuation-in-part of application No. 14/747,407, filed on Jun. 23, 2015, now abandoned.
(Continued)

(51) Int. Cl.
*A61N 1/36*     (2006.01)
*A61B 5/0478*     (2006.01)
(Continued)

(52) U.S. Cl.
CPC ...... *A61N 1/36025* (2013.01); *A61B 5/04001* (2013.01); *A61B 5/04012* (2013.01);
(Continued)

(58) Field of Classification Search
CPC .............. A61N 1/36025; A61B 5/04001; A61B 5/743; A61B 5/04012
(Continued)

(56) References Cited

U.S. PATENT DOCUMENTS

2007/0298821 A1    12/2007   Bush
2009/0082829 A1*   3/2009   Panken ............... A61B 5/7475
                                                                                      607/45
(Continued)

FOREIGN PATENT DOCUMENTS

| CN | 103845137 A | 6/2014 |
|---|---|---|
| WO | WO2014-036075 A1 | 3/2014 |
| WO | WO2015-153675 A1 | 10/2015 |

OTHER PUBLICATIONS

Ardekani B. A., Guckemus S., Bachman A., Hoptman M. J., Wojtaszek M., & Nierenberg J., Quantitative comparison of algorithms for inter-subject registration of 3D volumetric brain MRI scans. Journal of neuroscience methods, 142(1), pp. 67-76, 2005.
(Continued)

*Primary Examiner* — Amanda K Hulbert
*Assistant Examiner* — Philip C Edwards
(74) *Attorney, Agent, or Firm* — Tope-McKay & Associates

(57) ABSTRACT

Described is a system for inducing a desired behavioral effect using an electrical current stimulation. A brain monitoring subsystem includes monitoring electrodes for sensing brain activity, and a brain stimulation subsystem includes stimulating electrodes for applying an electrical current stimulation. Multi-scale distributed data is registered into a graphical representation. The system identifies a sub-graph in the graphical representation and maps the sub-graph onto concept features, generating a concept lattice which relates the concept features to a behavioral effect. Finally, an
(Continued)

electrical current stimulation to be applied to produce the behavioral effect is determined.

19 Claims, 11 Drawing Sheets

Related U.S. Application Data

(60) Provisional application No. 62/500,500, filed on May 3, 2017, provisional application No. 62/015,871, filed on Jun. 23, 2014.

(51) Int. Cl.
  *A61B 5/0484* (2006.01)
  *A61B 5/00* (2006.01)
  *A61B 5/04* (2006.01)
  *A61B 5/16* (2006.01)
  *A61N 1/02* (2006.01)
  *A61N 1/04* (2006.01)
  *A61N 1/05* (2006.01)

(52) U.S. Cl.
  CPC .......... *A61B 5/0478* (2013.01); *A61B 5/0484* (2013.01); *A61B 5/16* (2013.01); *A61B 5/743* (2013.01); *A61N 1/36031* (2017.08); *A61N 1/025* (2013.01); *A61N 1/0456* (2013.01); *A61N 1/0529* (2013.01); *A61N 1/36017* (2013.01); *A61N 1/36082* (2013.01)

(58) Field of Classification Search
  USPC .......................................................... 607/2
  See application file for complete search history.

(56) References Cited

U.S. PATENT DOCUMENTS

| | | | |
|---|---|---|---|
| 2009/0099627 A1* | 4/2009 | Molnar | A61B 5/04014 607/62 |
| 2013/0030317 A1* | 1/2013 | Tanner | A61B 5/0476 600/545 |
| 2014/0194945 A1 | 7/2014 | Stypulkowski et al. | |
| 2016/0000354 A1 | 1/2016 | Hagedorn et al. | |

OTHER PUBLICATIONS

Avants B. B., Cook P. A., Ungar L, Gee J. C., & Grossman M., Dementia induces correlated reductions in white matter integrity and cortical thickness: a multivariate neuroimaging study with sparse canonical correlation analysis. Neuroimage, 50(3), pp. 1004-1016, 2010.
Bak P., Tang C., & Wiesenfeld K., Self-organized criticality: An explanation of the 1/f noise. Physical review letters, 59 (4), pp. 381-384, 1987.
Barzel B., & Barabási A. L., Network Link Prediction by Global Silencing of Indirect Correlations. Nature biotechnology, 2013, pp. 720-725.
Chrysikou EG, Hamilton RH, Coslett HB, Datta A, Bikson M, Thompson-Schill SL. Noninvasive transcranial direct current stimulation over the left prefrontal cortex facilitates cognitive flexibility in tool use. Cogn Neurosci. 4(2): pp. 81-89, 2013.
Correa N. M., et al. Multi-set Canonical Correlation Analysis for the Fusion of Concurrent Single Trial ERP and Functional MRI, Neuroimage 50.4, pp. 1438-1445, 2010.
Dmochowski JP, Datta A, Bikson M, Su Y, Parra LC. Optimized multi-electrode stimulation increases focality and intensity at target. J Neural Eng. 8(4): pp. 046011 (16pp), 2011.
Freeman J., Vladimirov N., Kawashima T., Mu Y., Sofroniew N. J., Bennett D. V., & Ahrens M. B., Mapping brain activity at scale with cluster computing. Nature Methods, 11(9), pp. 941-950, 2014.
Hardoon D. R., and Shawe-Taylor J., Sparse Canonical Correlation Analysis, Machine Learning 83.3, pp. 331-353, 2011.
Hinton G.E., Salakhutdinov R.R., Reducing the Dimensionality of Data with Neural Networks, Science, 313: pp. 504-507, 2006.
Javadi AH, Cheng P. Transcranial direct current stimulation (tDCS) enhances reconsolidation of long-term memory. Brain Stimulation 6 (2013), pp. 668-674.
Javadi AH, Walsh V. Transcranial direct current stimulation (tDCS) of the left dorsolateral prefrontal cortex modulates declarative memory. Brain Stimulat., 5(3): pp. 231-241, 2012.
Marshall L, Helgadóttir H, Mölle M, Born J. Boosting slow oscillations during sleep potentiates memory. Nature. 444 (7119): pp. 610-613, 2006.
Miniussi C, Cappa SF, Cohen LG, Floel A, Fregni F, Nitsche MA, et al. Efficacy of repetitive transcranial magnetic stimulation/transcranial direct current stimulation in cognitive neurorehabilitation. Brain Stimulat. 1(4): pp. 326-236, 2008.
Ni, C. and Lu T-C., Information Dynamic Spectrum Characterizes System Instability toward Critical Transitions, EPJ Data Science, pp. 1-25, 2014.
Ramírez RR, Makeig S., Neuroelectromagnetic source imaging of spatiotemporal brain dynamical patterns using frequency-domain independent vector analysis (IVA) and geodesic sparse Bayesian learning (gSBL). 13th Annual Meeting of the Organization for Human Brain Mapping. Chicago, USA, 2007, p. 370.
Reis J, Schambra HM, Cohen LG, Buch ER, Fritsch B, Zarahn E, et al. Noninvasive cortical stimulation enhances motor skill acquisition over multiple days through an effect on consolidation. Proc Natl Acad Sci U S A. 106(5): pp. 1590-1595, 2009.
Sui, Jing, et al. A Review of Multivariate Methods for Multimodal Fusion of Brain Imaging Data., Journal of neuroscience methods 204.1, pp. 68-81, 2012.
Utz KS, Dimova V, Oppenlander K & Kerkhoff G. Electrified minds: transcranial direct current stimulation (tDCS) and galvanic vestibular stimulation (GVS) as methods of noninvasive brain stimulation in neuropsychology—a review of current data and future implications. Neuropsychologia. 48(10): pp. 2789-2810, 2010.
Wolters CH, Anwander A, Tricoche X, Weinstein D, Koch MA, MacLeod RS., Influence of tissue conductivity anisotropy on EEG/MEG field and return current computation in a realistic head model: A simulation and visualization study using high-resolution finite element modeling. Neuroimage 30(3): pp. 813-826, 2006.
Hoffmann H, Payton DW, Optimization by Self-Organized Criticality, Scientific Reports, Feb. 5, 2018, pp. 1-9.
Dmochowski JP, Koessler L, Norcia AM, Bikson M, Parra LC, Optimal use of EEG recordings to target active brain areas with transcranial electrical stimulation. Neuroimage 15;157: pp. 69-80, 2017.
Rodrigo, QQ, Spike sorting. Scholarpedia, 2(12): p. 3583, 2007.
Fletcher R, Powell MJ. A rapidly convergent descent method for minimization. The Computer Journal 1;6(2): pp. 163-168, 1963.
Optimization by Simulated Annealing. S. Kirkpatrick, C. D. Gelatt, Jr., M. P. Vecchi, Science, vol. 220, No. 1598, pp. 671-682, May 1983.
Self-Organized Criticality. Henrik Jeldtoft Jensen, Cambridge University Press, 1998. Chapter 3, pp. 12-28.
Self-Organized Criticality: An Explanation of 1/f Noise. P. Bak, C. Tang, K. Wiesenfeld, Physical Review Letters, vol. 59, No. 4, pp. 381-384, 1987.
Emergent Criticality in Complex Turing B-Type Atomic Switch Networks. A. Z. Stieg, A. V. Avizienis, H. O. Sillin, C. Martin-Olmos, M. Aono, J. K. Gimzewski, Advanced Materials, vol. 24, Issue 2, pp. 286-293, Jan. 10, 2012.
Theory of Quantum Annealing of an Ising Spin Glass. G. E. Santoro, R. Martonak, E Tosatti, R. Car, Science, vol. 295, pp. 2427-2430, Mar. 2002.
Office Action 1 for U.S. Appl. No. 14/747,407, dated Jul. 28, 2017.
Fernandes et al., "Self-Organized Critically Mutation Operator for Dynamic Optimization Problems" ACM GECCO '08, Jul. 12-16 2008, pp. 937-944.
Turcotte, "Self-organized Criticality" Rep. Prog. Phys. 62 (1999), pp. 1377-1429.

(56) References Cited

OTHER PUBLICATIONS

Response to Office Action 1 for U.S. Appl. No. 14/747,407, dated Nov. 28, 2017.
Office Action 2 for U.S. Appl. No. 14/747,407, dated Mar. 28, 2018.
Sun et al., "Population-based Extremal Optimization Algorithm for Hot Rolling Scheduling Problem" Journal of Computational Information Systems, vol. 6 No. 7, Jul. 2010, pp. 2415-2422.
Lassee, "Towards new Order" Presentation Dec. 3, 2003.
Notification of Transmittal of International Search Report and the Written Opinion of the International Searching Authority for PCT/US2018/028962; dated Aug. 9, 2018.
International Search Report of the International Searching Authority for PCT/US2018/028962; dated Aug. 9, 2018.
Written Opinion of the International Searching Authority for PCT/US2018/028962; dated Aug. 9, 2018.

* cited by examiner

METHOD AND APPARATUS TO DETERMINE OPTIMAL BRAIN STIMULATION TO INDUCE DESIRED BEHAVIOR

CROSS-REFERENCE TO RELATED APPLICATIONS

This is a Continuation-in-Part Application of U.S. Non-Provisional application Ser. No. 14/747,407, filed on Jun. 23, 2015, entitled, "System and Method for Determining a Plurality of States to Assign to Each of a Plurality of Actors," which is a Non-Provisional Application of U.S. Provisional Patent Application No. 62/015,871, filed on Jun. 23, 2014, entitled, "System and Method for Determining a Plurality of States to Assign to Each of a Plurality of Actors," the entirety of which are incorporated herein by reference.

This is also a Non-Provisional Application of U.S. Provisional Application No. 62/500,500, filed on May 3, 2017, entitled, "Method and Apparatus to Determine Optimal Brain Stimulation to Induce Desired Behavior," the entirety of which is incorporated herein by reference.

BACKGROUND OF INVENTION

(1) Field of Invention

The present invention relates to a system for inducing a desired behavior and, more particularly, to a system for inducing a desired behavior using a determined brain stimulation.

(2) Description of Related Art

The state-of-the-art to discover invasive and non-invasive stimulation patterns to enhance a particular behavioral function is essentially based on an expensive experimental process of trial and error. For example, if there are 8 scalp electrodes and 20 possible locations with 10 levels of intensity and 5 levels of frequency for non-invasive stimulation, then one would need U.S. Pat. No. 6,298,500 trials to determine the best stimulation montage for a subject in a brute-force way.

A system for fast analysis of large-scale neural data, known as THUNDER (see the List of Incorporated Literature References, Literature Reference No. 8), is mostly just capable of finding the subset of cells that are modulated by some aspect of stimulus/behavior. Simulated annealing, which is state-of-the-art for hard optimization problems with many local minima, requires tedious tuning of annealing parameters. It is slow and must be restarted from scratch when the optimization target moves.

Behavioral enhancement has been attempted with weak current stimulation, guided by a coarse understanding of the underlying neural processes (such as described in Literature Reference Nos. 14 and 19) and typically involves targeting the stimulation to just the prefrontal cortex (PFC) in general (see Literature Reference Nos. 5, 11, 12, and 13), or one or two brain regions known to be specialized for the particular behavior (see Literature Reference No. 17), or identified by a clinician (see Literature Reference No. 7).

No prior art methods exist to produce any desired behavioral effect. Thus, a continuing need exists for a method to compute the most optimal stimulation application based on available data from experiments that have already been conducted without the requirement for trial-and-error procedures.

SUMMARY OF INVENTION

The present invention relates to a system for inducing a desired behavior and, more particularly, to a system for inducing a desired behavior using a determined brain stimulation. The system comprises a brain monitoring subsystem comprising a set of monitoring electrodes for sensing brain activity, and a brain stimulation subsystem comprising a set of stimulating electrodes for applying an electrical current stimulation. The system further comprises one or more processors and a non-transitory computer-readable medium having executable instructions encoded thereon such that when executed, the one or more processors perform multiple operations. A set of multi-scale distributed data is registered into a graphical representation, wherein at least a subset of the set of multi-scale distributed data is sensed brain activity. A sub-graph is identified in the graphical representation and mapped onto a set of concept features, generating a concept lattice which relates the set of concept features to a behavioral effect. The system then determines an electrical current stimulation to be applied to produce the behavioral effect and causes the electrical current stimulation to be applied via the set of stimulating electrodes.

In another aspect, the graphical representation comprises a plurality of nodes, each node representing a data item in the set of multi-scale distributed data, and edges between the plurality of nodes representing relationships between data items, wherein the relationships are topological, statistical, and/or causal relationships.

In another aspect, the set of multi-scale distributed data comprises electroencephalogram data recorded from the set of monitoring electrodes as a result of the stimulation montage applied via the set of stimulating electrodes.

In another aspect, the set of multi-scale distributed data is transformed through a forward simulation into currents in voxels of brain volume, and the currents are integrated into the graphical representation.

In another aspect, a set of stimulating electrode placements and parameters that can recreate the behavioral effect is identified.

In another aspect, the identified set of stimulating electrode placements and parameters are applied via the brain stimulation subsystem, and wherein the brain monitoring subsystem monitors the behavioral effect, wherein if the behavioral effect is unsatisfactory, then the brain monitoring subsystem updates the graphical representation and the one or more processors perform an operation of determining a new electrical current stimulation to be applied to produce a satisfactory behavioral effect.

In another aspect, self-organized criticality (SOC) is used to search for electrode locations or settings for brain stimulation.

In another aspect, a forward simulation is used to predict behavioral outcomes for various brain stimulations.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
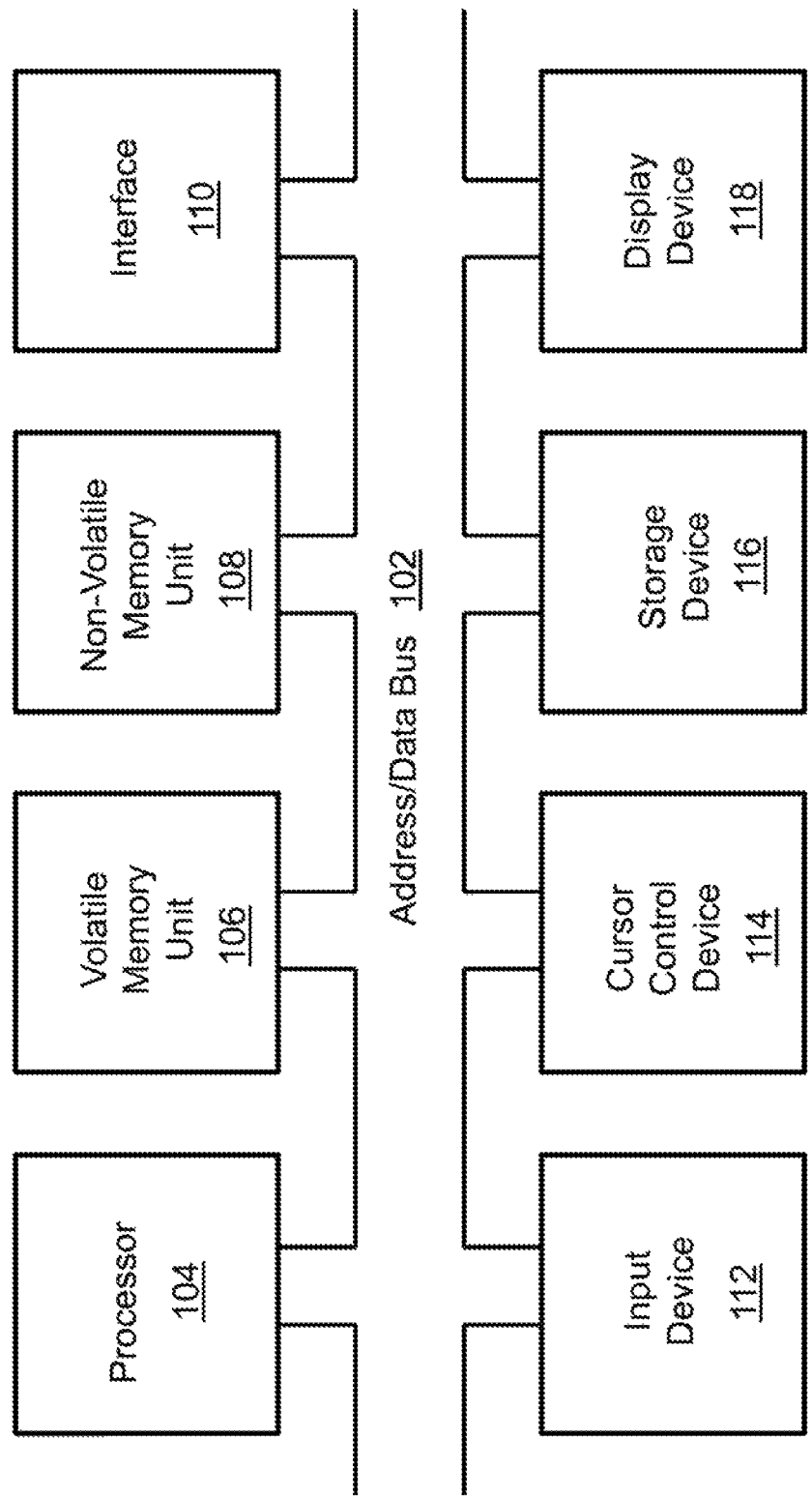
FIG. 1 is a block diagram depicting the components of a system for inducing a desired behavior according to some embodiments of the present disclosure.

The present invention relates to a system for inducing a desired behavior and, more particularly, to a system for inducing a desired behavior using a determined brain stimulation.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) List of Incorporated Literature and Patent References

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number.

1. Ardekani B. A., Guckemus S., Bachman A., Hoptman M. J., Wojtaszek M., & Nierenberg J., Quantitative comparison of algorithms for inter-subject registration of 3D volumetric brain MRI scans. Journal of neuroscience methods, 142(1), 67-76, 2005.
2. Avants B. B., Cook P. A., Ungar L. Gee J. C., & Grossman M Dementia induces correlated reductions in white matter integrity and cortical thickness: a multivariate neuroimaging study with sparse canonical correlation analysis. Neuroimage, 50(3), 1004-1016, 2010.
3. Bak P., Tang C., & Wiesenfeld K., Self-organized criticality: An explanation of the 1/f noise. Physical review letters, 59(4), 381, 1987.
4. Barzel B., & Barabási A. L., Network Link Prediction by Global Silencing of Indirect Correlations. Nature biotechnology, 2013.
5. Chrysikou E G, Hamilton R H, Coslett H B, Datta A, Bikson M, Thompson-Schill S L. Noninvasive transcranial direct current stimulation over the left prefrontal cortex facilitates cognitive flexibility in tool use. Cogn Neurosci. 4(2):81-9, 2013.
6. Correa N. M., et al. Multi-set Canonical Correlation Analysis for the Fusion of Concurrent Single Trial ERP and Functional MRI, Neuroimage 50.4, 1438-1445, 2010.
7. Dmochowski J P, Datta A, Bikson M, Su Y, Parra L C. Optimized multi-electrode stimulation increases focality and intensity at target. J Neural Eng. 8(4):046011, 2011.
8. Freeman J., Vladimirov N., Kawashima T., Mu Y., Sofroniew N. J., Bennett D. V., & Ahrens M. B., Mapping brain activity at scale with cluster computing. Nature Methods, 11(9), 941-950, 2014.
9. Hardoon D. R., and Shawe-Taylor J., Sparse Canonical Correlation Analysis, Machine Learning 83.3, 331-353, 2011.
10. Hinton G. E., Salakhutdinov R. R., Reducing the Dimensionality of Data with Neural Networks, Science, 313:5786, 2006.

11. Javadi A H, Cheng P. Transcranial direct current stimulation (tDCS) enhances reconsolidation of long-term memory. Brain Stimulation, 2012.
12. Javadi A H Walsh V. Transcranial direct current stimulation (tDCS) of the left dorsolateral prefrontal cortex modulates declarative memory. Brain Stimulat., 5(3):231-41, 2012.
13. Marshall L, Helgadóttir H, Mölle M, Born J. Boosting slow oscillations during sleep potentiates memory. Nature. 444(7119):610-3, 2006.
14. Miniussi C, Cappa S F, Cohen L G, Floel A, Fregni F, Nitsche M A, et al. Efficacy of repetitive transcranial magnetic stimulation/transcranial direct current stimulation in cognitive neurorehabilitation. Brain Stimulat. 1(4): 326-36, 2008.
15. Ni, C. and Lu T-C., Information Dynamic Spectrum Characterizes System Instability toward Critical Transitions, EPJ Data Science, In Press, 2014.
16. Ramirez R R, Makeig S., Neuroelectromagnetic source imaging of spatiotemporal brain dynamical patterns using frequency-domain independent vector analysis (IVA) and geodesic sparse Bayesian learning (gSBL). 13th Annual Meeting of the Organization for Human Brain Mapping, Chicago, USA, 2007.
17. Reis J, Schambra H M, Cohen L G, Buch E R, Fritsch B, Zarahn E, of al. Noninvasive cortical stimulation enhances motor skill acquisition over multiple days through an effect on consolidation. Proc Natl Acad Sci USA. 106(5):1590-5, 2009.
18. Sui, Jing, et al. A Review of Multivariate Methods for Multimodal Fusion of Brain Imaging Data., Journal of neuroscience methods 204.1, 68-81, 2012.
19. Utz K S, Dimova V, Oppenländer K & Kerkhoff G. Electrified minds: transcranial direct current stimulation (tDCS) and galvanic vestibular stimulation (GVS) as methods of noninvasive brain stimulation in neuropsychology a review of current data and future implications. Neuropsychologia. 48(10):2789-810, 2010.
20. Wolters C H, Anwander A, Tricoche X, Weinstein D, Koch M A, MacLeod R S., Influence of tissue conductivity anisotropy on EEG/MEG field and return current computation in a realistic head model: A simulation and visualization study using high-resolution finite element modeling, Neuroimage 30(3):813-826, 2006.
21. Hoffmann Payton D W, Optimization by Self-Organized Criticality, Scientific Reports, Feb. 5, 2018.
22. Dmochowski J P, Koessler L, Norcia A M, Bikson M, Parra L C, Optimal use of EEG recordings to target active brain areas with transcranial electrical stimulation. Neuroimage 157:69-80, 2017.
23. Rodrigo, Q Q, Spike sorting. Scholarpedia, 2(12): 3583, 2007.
24. Fletcher R., Powell M J. A rapidly convergent descent method for minimization. The Computer Journal 1; 6(2): 163-8, 1963.

(2) Principal Aspects

Various embodiments of the invention include three "principal" aspects. The first is a system for inducing a desired behavior. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
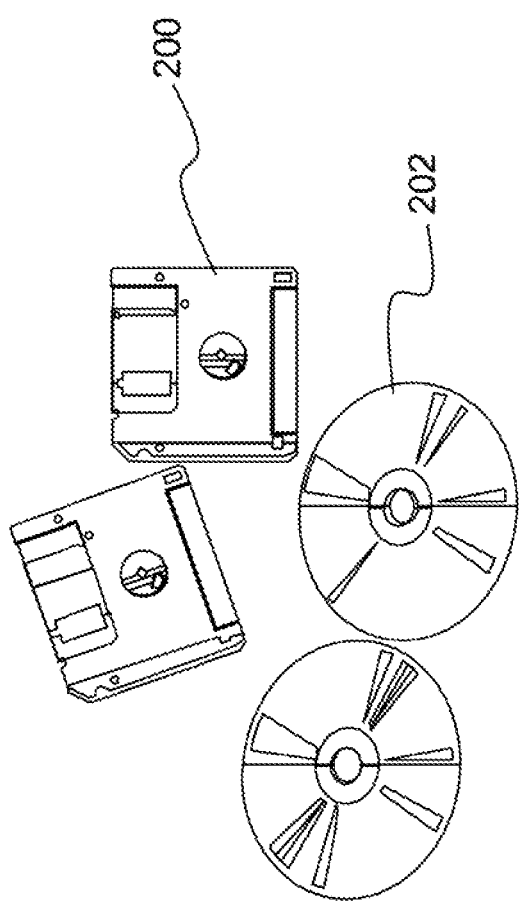
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of Various Embodiments

Described is a system to discover the relationships between neural activity, applied current stimulation, and behavioral performance (such as memory enhancement) from neural data (e.g., produced by programs such as DARPA (Defense Advanced Research Projects) RAM (Restoring Active Memory) and SUBNETS (Systems-Based Neurotechnology for Emerging Therapies) and to compute the optimal brain stimulation montage for an individual subject, or across the general population, that will produce a desired behavioral effect. Non-limiting examples of desired behavioral effects include enhancement of selected memories (e.g., beneficial for task performance) and weakening of selected memories (e.g., those that cause trauma or harm task performance). The system runs closed-loop, monitoring the brain, computing and applying new stimulation patterns, and improving the behavioral effect on each round until the desired effect is achieved. A unique element of the system described herein is a forward model to predict behavioral outcomes for different stimulations, and the use of a search method as an optimization technique to identify the ideal stimulation pattern to produce a desired behavioral outcome.

There are many brain stimulation systems currently on the market, but none of them provide a forward model that can predict the behavioral effect of a certain stimulation montage. This prediction makes the system according to embodiments of the present disclosure different from prior art and advances the science of brain stimulation from a hunch, based on the still primitive understanding of brain function, to an informed analytical optimization. Although the invention described herein can be used as an intelligent closed-loop stimulation system, the forward model upon which the invention is based can also provide answers to clearly definable queries, such as "What are the essential brain attributes underlying a given behavioral outcome?" and "Which brain stimulation patterns lead to an improvement of a specific behavior?"

Understanding brain function involves large volumes of multi-modal data, ranging in spatial scales from single neuron spiking activity to local field potentials and electroencephalogram (EEG) signals. The data also ranges widely in temporal scales from low-frequency to high-frequency spectral interactions among various neural entities. The method according to embodiments of the present disclosure includes techniques to register, across subjects and within subjects across trials, the multi-scale distributed neural data as well as the induced current flow distributions in the brain volume. For optimization, a recently discovered method self-organized critical (SOC) search (see Literature Reference No. 21 for a description of SOC search), which solves high-dimensional optimization problems about 8× faster than simulated annealing, was adapted and used to solve the inverse problem of determining optimal stimulation patterns that can induce current flows in the brain volume for certain behavioral states across trials and also across subjects. Each of these aspects will be described in further detail below.

(3.1) Overview

Figure 3:
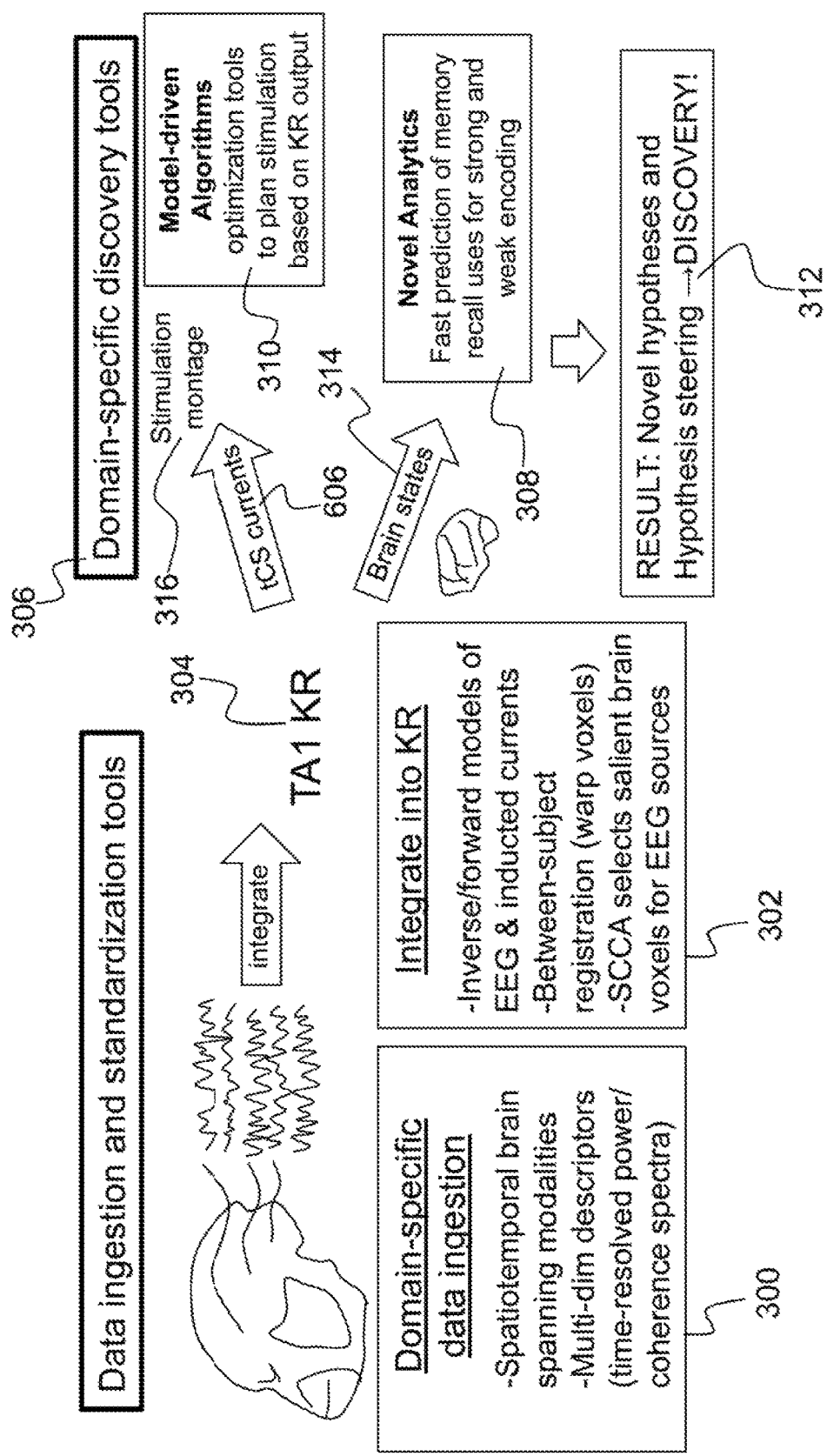
FIG. 3 is an illustration of an overview of discovering a stimulation pattern that can produce a desired behavior according to embodiments of the present disclosure.

FIG. 3 illustrates how the system described herein is applied to discover a stimulation pattern that can produce a desired behavior. Datafication (i.e., domain-specific data ingestion 300) extracts and ingests relevant experimental and computational data, comprising both quantitative and qualitative elements, and integrates them into a knowledge representation (KR) 302. Datafication includes making pairwise topological, statistical, and causal relations within the data and composing them into multilayer graphs, each annotated with qualitative and quantitative information of experimental designs. Datafication tools are capable of extracting time-varying multi-scale correlational and causal interactions among the identified neural entities, to facilitate a deeper discovery of the functional connectivity underlying behavior. Datafication refers to converting phenomena or data into a computable format that aids in the extraction of knowledge.

The KR 304 outputs ranked-ordered hypotheses to domain-specific discovery tools/datafication tools 306 (described in detail below), to further guide experimental design and computational data analysis with domain-specific computational models. Non-limiting examples of domains include complex domains with large datasets like neuroscience, climate science, gene-protein disease networks, smart power grids, wireless communication systems, and autonomous systems. These tools analyze and perform function inferences for fast brain classification to predict memory behavior (element 308) as well as optimization of stimulation patterns for memory enhancement (element 310).

Figure 4:
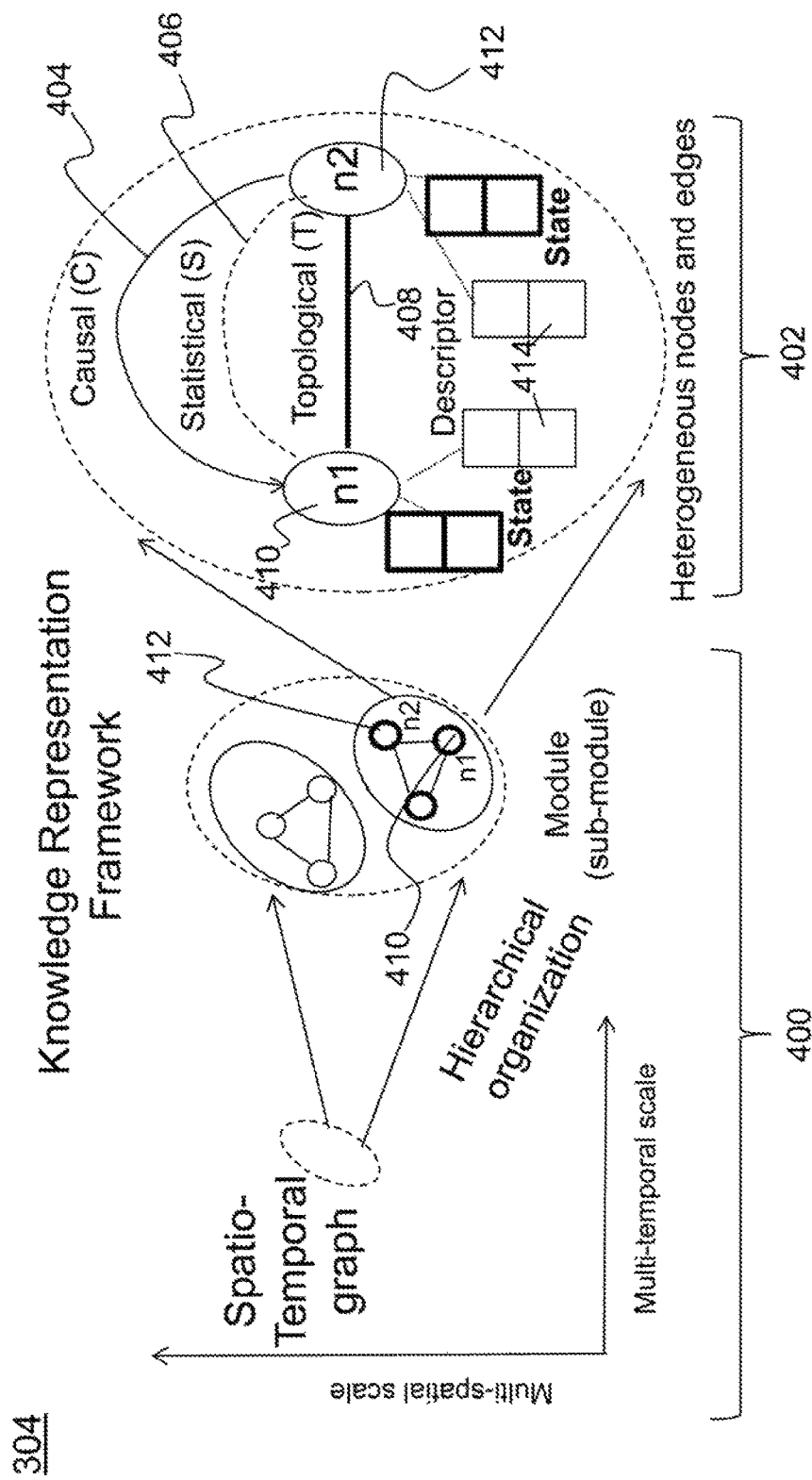
FIG. 4 is an illustration of a knowledge representation framework according to embodiments of the present disclosure.
Figure 5:
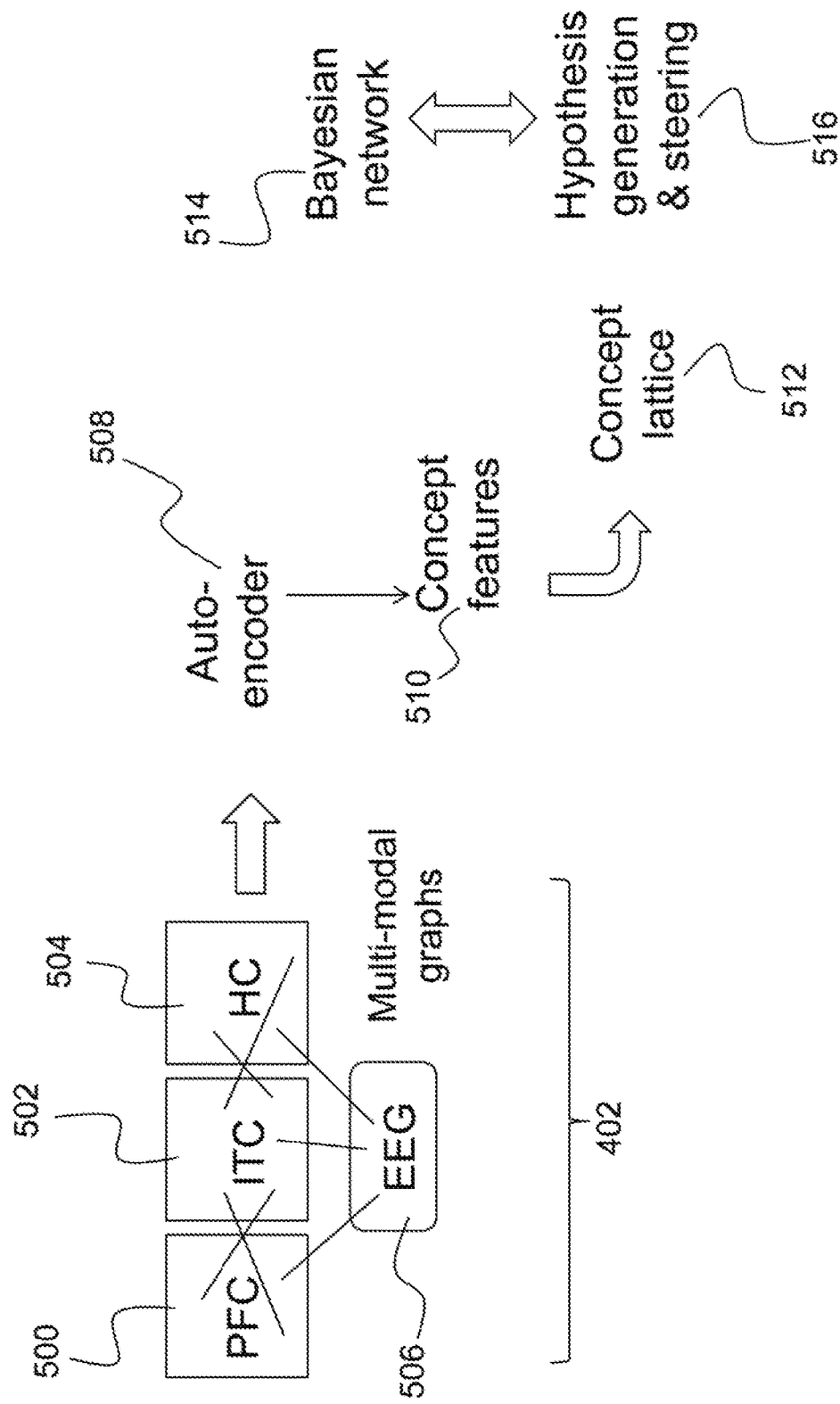
FIG. 5 is an illustration of generation of hypotheses on a lattice and Bayesian network according to embodiments of the present disclosure.
Figure 8:
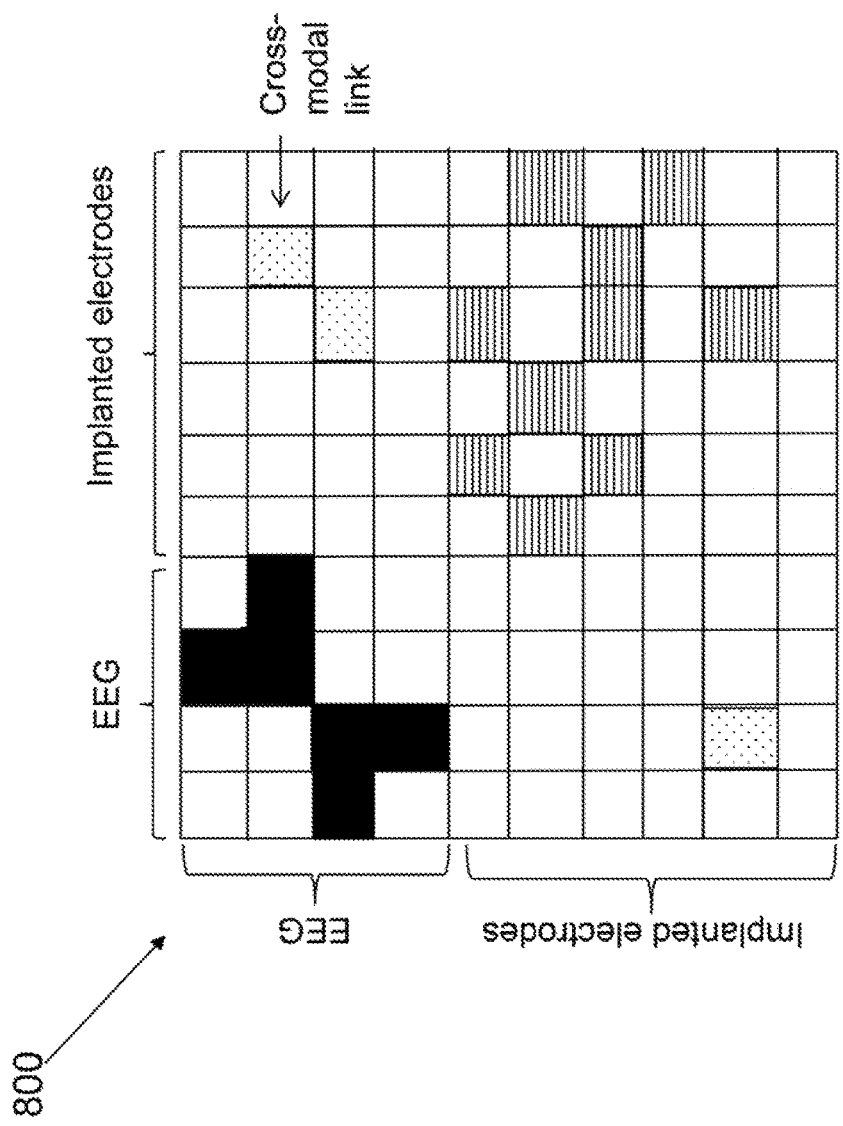
FIG. 8 is an illustration of a signal graph according to embodiments of the present disclosure.

Multimodal data can be described within a signal graph, such as shown in FIG. 8, or across a multitude of annotated graphs, such as shown in FIG. 4. FIG. 8 illustrates the adjacency matrix of a graph representation, which can capture intra-model and cross-model links. As depicted in FIG. 5, after identifying local regions in these graphs, autoencoders (element 508) compute concept features for the concept lattice 512 and Bayesian networks 514. An autoencoder, as known to those skilled in the art, is a recurrent network used for unsupervised learning of efficient codings. The aim of an encoder is to learn a representation (encoding) for a set of data, typically for the purpose of dimensionality reduction. Hypotheses (element 516) can then be generated on the concept lattice 512 and the Bayesian network 514 and retrieve corresponding entities, relations, and functions from the multilayer graphs (FIG. 5).

For instance, if the data domain is neuroscience, hypotheses may be which neural signatures (among the huge amount of available data from EEG and implanted electrodes, over time and across subjects) underlie successful memory encoding. If the data domain is property prediction in materials science, the hypotheses may be which set of material properties can be synthesized to achieve the ideal behavior of each, to discover new polymeric materials with desired properties from historical experimental and computational data of polymer formulation and monomer constituents.

(3.2) Datafication

FIG. 4 depicts source data from EEG or invasive electrodes (converted into spatiotemporal graphs 400) compiled into a graph-based representation 402 of causal (element 404), statistical (element 406), and topological (element 408) relationships between neural data. Raw brain data is processed and converted into cross-modal spatiotemporal graphs (element 400) corresponding to memory networks in the brain. These networks are subregions of the brain believed to be most responsible for the behavior of interest, which, for memory performance, includes regions of the hippocampus, the inferotemporal lobe, and the prefrontal cortex.

For data recorded from invasive electrodes (iCS, for invasive current stimulation), the nodes (depicted as circles (e.g., n1 410 and n2 412) in the graph will be voltage traces from single neurons and local field potentials (LFPs) extracted from extracellular recordings with implanted microelectrode arrays in the brain areas of interest, using standard frequency filtering, spike sorting, and source separation techniques. Frequency filtering is a standard technique that means taking the power spectral density of the EEG, which gives the power in the signal as a function of frequency. For a description of spike sorting techniques, refer to Literature Reference No. 23. For a description of source separation techniques, refer to Literature Reference No. 22. For data recorded from non-invasive electrodes (tCS, for transcranial current stimulation), the nodes (elements 410 and 412) correspond to current sources from scalp EEG signals mapped into voxels in a standardized brain volume. The links between the nodes, within and between modalities, are of different kinds related to the underlying statistical (element 406) and causal (element 404) relations.

Statistical links (element 406) are represented using the time-resolved coherence spectra, which capture the time-varying multi-scale correlational structure for pairs of time series. Time-variant causal links (element 404) are computed using a robust version of the transfer entropy measure, which essentially quantifies the conditional mutual information between two random processes across multiple time scales and invariant to their relative amplitudes. EEG sources and stimulation-induced currents are mapped to brain voxels using a forward model, and labeled to provide qualitative data for use in building hierarchical clusters in the graph and also enable discoveries in terms of functional interactions among specific brain regions.

The instantiation of these brain networks is informed by state-of-the-knowledge in neurophysiology (i.e., by one skilled in the art) to limit graph structure to meaningful and interpretable relations, especially those between the invasive and non-invasive modalities (e.g., LFP-EEG links, and not spike-EEG links), and to use knowledge about brain region functional specialization to inform the clustering. Multidimensional node and link properties are compressed into relevant features using stacks of autoencoders 508, as described in Literature Reference No. 10) with data registered across trials and subjects. An autoencoder 508 is an artificial neural network used for unsupervised learning of efficient codings. An autoencoder learns a representation (or encoding) for a set of data. In the invention described herein, autoencoders 508 are used for dimensionality reduction.

As shown in FIG. 5, once the graph-based representation 402 (or relationship graph) is prepared (here, the topological relations fall into brain subregions prefrontal cortex 500 (PFC), infero-temporal cortex 502 (ITC), hippocampus 504 (HC) as assessed by EEG 506), autoencoders 508 are run on local regions of the graph-based representation 402, forming compact concept features 510 (or representations) that are arranged into a concept lattice 512, which is searched (i.e., by SOC search) to find the most relevant areas to be stimulated to produce a desired behavioral effect.

(3.2.1) Time-Resolved Power and Coherence Spectra (Element 406)

The statistical relationship graphs (graphical representation 402) are created by using a wavelet transform to compute time-varying properties of identified entities as well as those of statistical relations (element 406) between them in the various neural and non-neural modalities. For coherence spectra, the time series at either node are first convolved by a family of complex Morlet's wavelets w(t, f), one for each frequency, as a function of time:

$$w(t, f) = Ae^{-\frac{t^2}{2\sigma_t^2}} e^{j2\pi ft},$$

in which the standard deviation of the Gaussian envelope $\sigma_t$ is inversely proportional to frequency f, and coefficient A is set such that total energy of each wavelet is equal to 1. The complex conjugate of one of the outputs is then multiplied element-wise with the other to obtain the coherence spectra. This is equivalent to the time-resolved Fourier spectrum of the cross-correlation between the two time series. The time-resolved power spectrum is similarly computed, the difference being just that it is linked to autocorrelation.

(3.2.2) Scale-Invariant Transfer Entropy (Element 404)

The time-varying causal links (element 404) are quantified in the multi-modal graph/graphical representation (element 402) using the transfer entropy (TE) metric, which is essentially a directional measure of information flow between a pair of time series:

$$TE_{x_j \to x_i}(t) = \sum p(x_{i,t+\tau}, x_{i,t}, x_{j,t}) \log \frac{p(x_{i,t+\tau} | x_{i,t}, x_{j,t})}{p(x_{i,t+\tau} | x_{i,t})},$$

where τ is the time delay of information transfer. The above equation computes the transfer entropy from node j to node i (the information flow across the link from node xj to xi). p is a Bayesian operator that assesses the probability that the quantity in parentheses is true. The TE at each time point t depends on the duration T over which the information transfer is considered, and also on the choice of τ. As the memory use case is defined by multi-modal multi-scale brain measurements, it would be challenging to specify an optimal τ value globally. However, the duration T can be assumed to be 100 milliseconds (ms) given the typical frequency of the dominant θ rhythm (namely, 10 Hertz (Hz)) in the LFPs within memory circuits in the brain. Therefore, TE is computed at a spectrum of time delays, spanning the assumed duration T of 100 ms.

The system described herein also incorporates a recently developed associative transfer entropy (ATE) notion that extends TE to distinguish the types of information being transferred by decomposing the associated states (see Literature Reference No. 15). A simple example is to distinguish between positive causal effects and negative causal effects, rather than just obtaining the total causal effects. ATE decomposes TE by constraining a particular associated state S into a subset of the set of all possible states $\{(x_{i,t+\tau}, x_{i,t}, x_{j,t})\}$, which allows one to quantify the amount of specific information transfer.

TE and ATE are computed through a scale-invariant symbolization method to remove any temporal scale dependencies. The formulations of TE and ATE are defined on continuous random variables, which are discretized by using a symbolization method to estimate their probability distributions. The key step is to transform the continuous-valued time series $\{x_t\}$ into a symbolic time series with a suitable length n. For each time point t, the n consecutive values $\{x_t, x_{t+1}, \ldots, x_{t+n-1}\}$ are ordered in the ascending order. The sequence of corresponding permutation indices is then the $t^{th}$ element for the discrete-valued symbolic time series $\{\hat{X}_t\}$.

(3.2.3) Global Silencing of Indirect Links

A substantial number of spurious statistical and causal links (elements 406 and 404) within each brain area for the invasive modality would be instantiated based on spurious relations, and can be suppressed. For instance, a causal link (element 404) from A to C may be falsely inferred in the network A→B→C, even though there is no direct path from A to C. For this, the system according to embodiments of the present disclosure builds upon prior art (see Literature Reference No. 4) to address the challenge of graphs with multi-dimensional node and link properties. For each link type and feature descriptor 414, a matrix G is constructed that represents the structure of a local network in a brain area under consideration. The technique described in Literature Reference No. 4 operates on the correlation matrix G to preserve the direct links while silencing the indirect links for a simpler graph structure by exploiting the implicit flow of information in the network by computing:

$$S=(G-I+D((G-I))G^{-1},$$

where I is the identity matrix, and D(M) sets the off-diagonal terms of M to zero.

(3.2.4) Registration (Element 302)

In order to register both measured and induced data for the non-invasive modality, a unique application of state-of-the-art forward and inverse models as well as warping techniques is used. Registration of scalp EEG signals across subjects is typically ensured by using a standard EEG cap with a stereotypical layout for electrode locations (such as a 10-20 or a 10-10 system), where the spacing between adjacent electrodes is proportional to individual head dimensions. However, in the memory use case described herein, the EEG electrode locations for the different subjects are not registered because of the practical issue that it is impossible to implant electrodes the same in different subjects; the data are constrained by the positions of ports for sensor arrays.

Additionally, for implanted arrays, EEG is recorded from the same electrodes used for transcranial current stimulation (tCS), so their locations further change between trials to optimize a specific stimulation pattern. To solve this registration challenge, first, EEG signals (time series) are converted into volumetric and temporal dynamics of current density sources within gray matter voxels in the brain, segmented from T1-weighted MRI for each individual subject, using state-of-the-art methods for source localization. Specifically, a subject-specific forward model is built using finite element modeling (see Literature Reference No. 20, which describes how to build a forward model using the technique of forward element modeling) and an inverse model using multi-scale geodesic Sparse Bayesian learning (SBL) with a Laplacian prior (see Literature Reference No. 16, which describes how to build an inverse model using SBL with a Laplacian prior), which is widely regarded as being appropriate for localizing distributed sources in the domain of non-invasive imaging. These models make the problem of registering between subjects more tractable, given state-of-the-art methods for warping structural and functional MRI data into a standard brain template. In particular, the nonlinear non-parametric automatic registration toolbox (ART) package is leveraged, which has been shown to outperform other methods in terms of reduced anatomical variability across subjects (see Literature Reference No. 1).

A similar issue is registering non-invasive stimulation montages between trials in which stimulation is applied and also between subjects. For this, a subject-specific forward model for high-resolution stimulation-induced current flows was built using finite element modeling and segmentation of the anatomical MRI (T1) of each individual subject into different tissue categories (e.g., brain, skull, cerebrospinal fluid (CSF), electrode), based on pertinent state-of-the-art methods (see Literature Reference No. 7). Then, the aforementioned ART package will register the induced currents within the brain volume between subjects. In this way, the present system's solution can deal with arbitrary locations of scalp electrodes for non-invasive stimulation.

(3.2.5) Dimensionality Reduction (Element 302)

Figure 9:
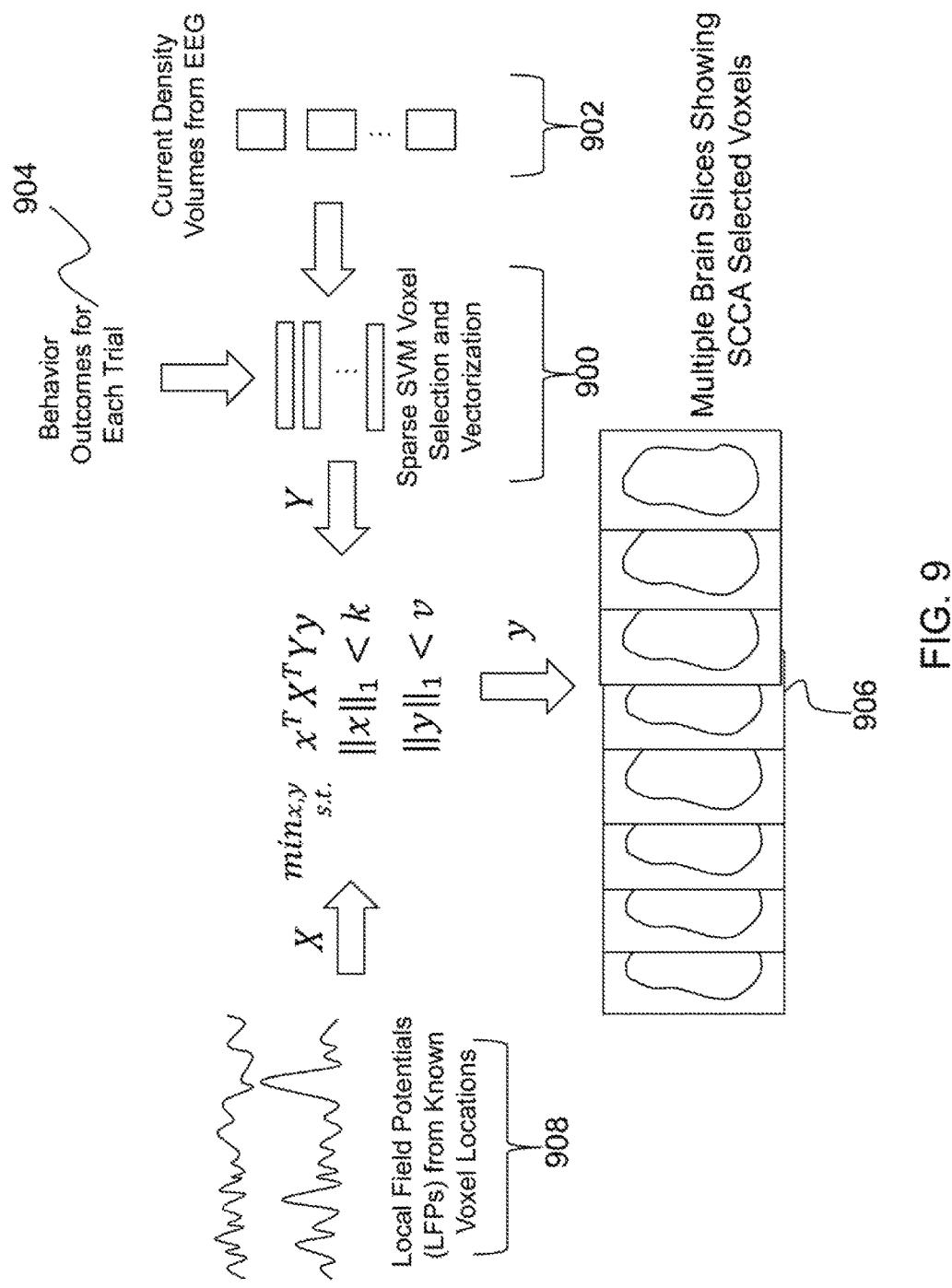
FIG. 9 is an illustration of leveraging sparse support vector machine (SVM) and sparse canonical correlational analysis (SCCA) for dimensionality reduction according to embodiments of the present disclosure.

A unique dimensionality reduction method is employed for the challenging datafication of EEG signals obtained from different scalp electrode placements across subjects. "Datafication" refers to converting phenomena or data into a computable format that aids in the extraction of knowledge. Given that the number of voxels in the transformed EEG data is much greater than the number of actual electrode channels, it is likely that EEG-derived current density source images are noisy. Additionally, the number of voxels is large enough to be prohibitive for instantiating a graph for the EEG modality. To solve these coupled problems, an innovative tool that leverages sparse support vector machine (SVM) and sparse canonical correlational analysis (SCCA) for dimensionality reduction was employed. FIG. 9 depicts that a sparse SVM sub-selects discriminative voxels (element 900) from the EEG-derived current density volumes (element 902) based on the outcome of each behavioral trial (element 904), and then Sparse Canonical Correlation Analysis (SCCA) determines a further subset of voxels (element 906) that are maximally correlated with the known voxel locations of invasive LFP recordings (element 908).

Thus, the subset of most salient voxels is determined in two steps: first selecting the voxels that are maximally discriminative between successful and failed memory recall outcomes in the corresponding retrieval trials (using sparse SVM (element 900); and then further down-selecting based on maximizing the overall correlation with simultaneously recorded local field potential data (element 908) in the three brain areas (using SCCA (element 906)).

For the second step, the SCCA will project the current density estimates for the discriminative set of voxels and the spatially localized LFPs (element 908) onto a common feature space in order to determine the semantics of the underlying neuronal activity patterns. From these semantics, SCCA will learn the subset of voxels for the EEG sources (Y) whose time series are maximally correlated with the time series from the low-dimensional ground truth of the invasive LFP measurements (X). The addition of sparsity constraints to the SCCA mitigates the influence of outlier EEG source estimates in the neuronal data and is appropriate when many voxels are likely to be uninformative for neural decoding (see Literature Reference No. 2). Sparse SVMs successfully reduce feature dimensionality 50× to 100× while maintaining high levels of classifier precision.

SCCA is a robust scale-invariant method that can readily be extended to use kernel methods to accommodate non-linear relationships between LFPs (element 908) and EEG source estimates (element 902) (see Literature Reference No. 9), feature learning over multiple subjects for increased statistical power (see Literature Reference No. 6), and Independent Component Analysis (ICA) if it is determined the model for multiple subject analysis requires feature independence within subjects but feature correlation between them (see Literature Reference No. 18). This is the first instance of SCCA (element 906) being used to determine a spatiotemporal mapping between invasive LFPs (element 908) and inferred current density sources from non-invasive EEG signals (element 902).

(3.3) Discovery (Element 312)

The unique analytics and discovery tools of the system according to embodiments of the present disclosure ingest outputs from the datafication system described above in response to queries for brain attributes in a specific modality and also for stimulation-induced currents that are linked in high-level concept space to the behavioral outcome of strong memory encoding. This section elaborates how these tools can help to discover optimal stimulation montages to facilitate behavioral enhancement.

FIG. 5 depicts turning the processed data into a concept lattice 512, and then the lattice is searched to find the best behavioral results and identify the concepts that represent the brain state (element 314) desired. Recall that those concept features 510 consist of auto-encoded (element 508) portions of the input data graph (element 402), and, thus, identify the target brain state (element 508) of individual brain voxels. Once the desirable brain states (element 314) are known, the key functional inference challenge is solving the hard high-dimensional inverse mapping problem of estimating the stimulation pattern, either applied invasively or non-invasively, that induces a particular current density distribution within the brain volume.

(3.3.1) Optimal Stimulation for Memory Enhancement (Element 310)

Figure 10:
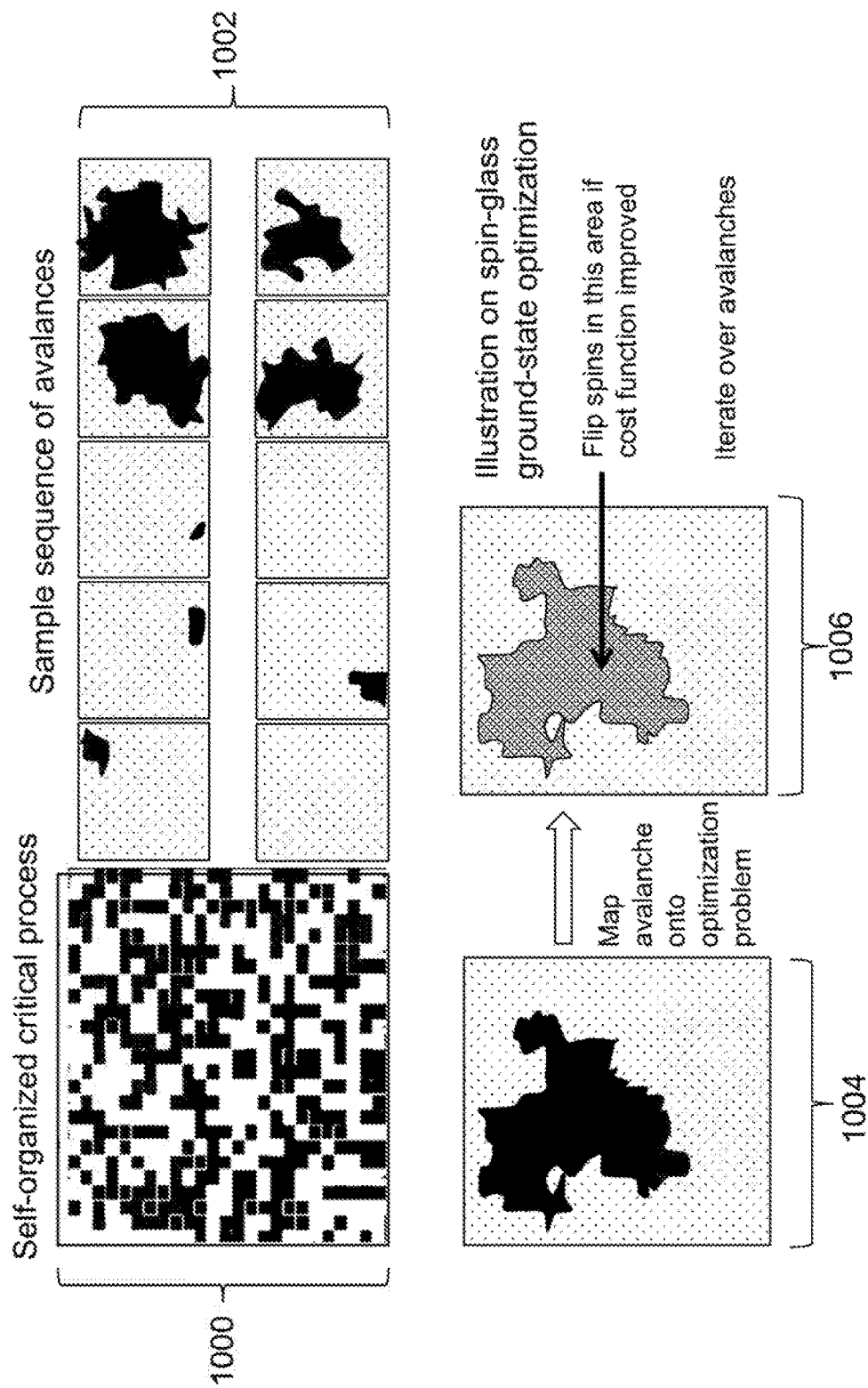
FIG. 10 is an illustration of using self-organized critical (SOC) search according to embodiments of the present disclosure.

As shown in FIG. 10, self-organized critical (SOC) search is used to solve the inverse problem of estimating invasive and non-invasive neurostimulation montages that induce an arbitrary distribution of current densities through the brain volume. For further details regarding SOC search, refer to Literature Reference No. 21 and U.S. application Ser. No. 14/747,407, which is hereby incorporated by reference as though fully set forth herein.

Figure 6:
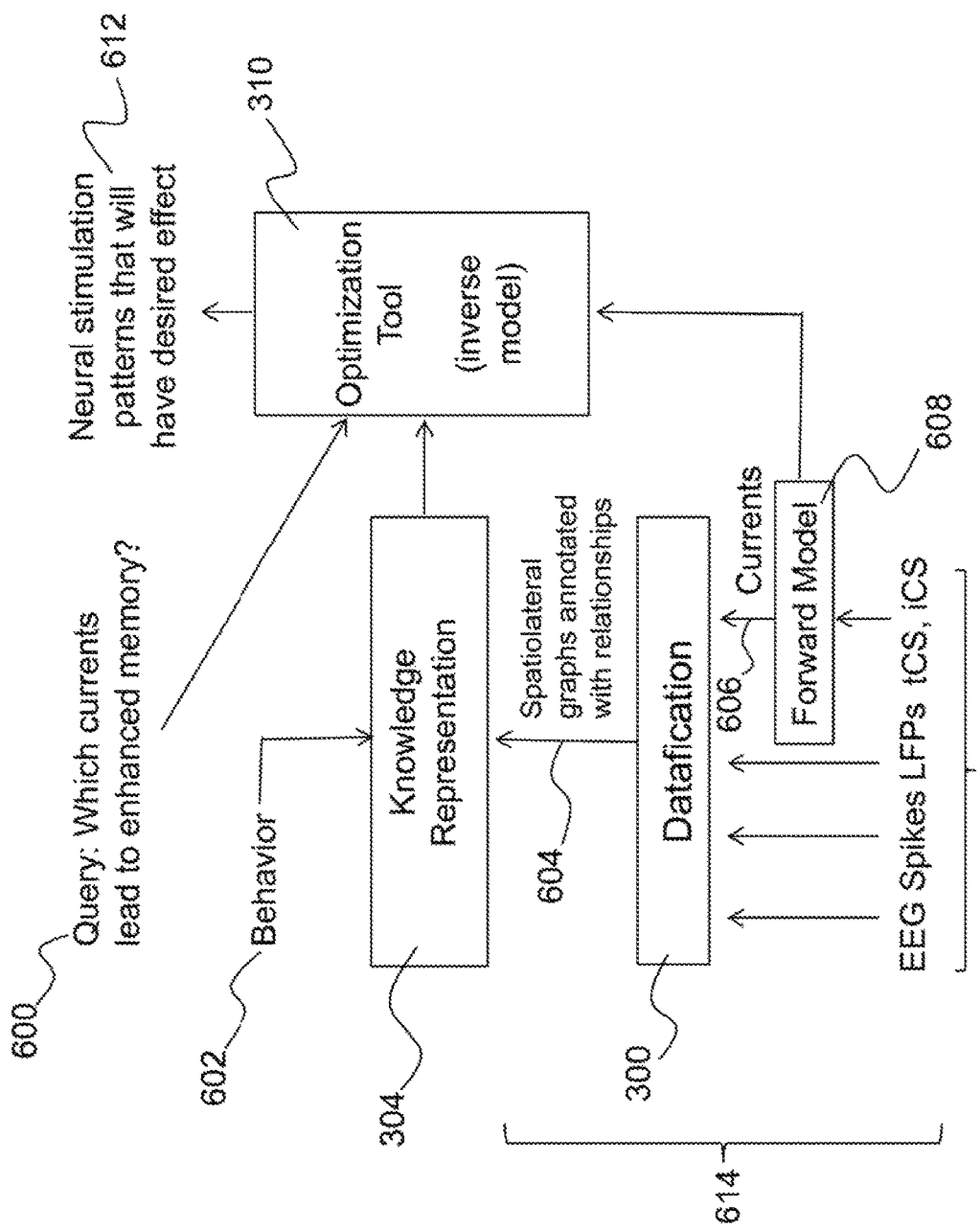
FIG. 6 is a flow diagram illustrating the system for inducing a desired behavior according to embodiments of the present disclosure.

As depicted in FIG. 6, the KR systems 304 discover and extract signature templates of stimulation-induced currents based on queries (element 600) related to behavioral phenomena of interest (e.g., strong memory encoding) (element 602). For instance, a query (element 600) may be in the form: "Which currents lead to enhanced memory?" This is possible because the KR system 304 ingests experimental data related to memory retrieval outcomes and associated multi-modal multi-scale brain measurements (i.e., spatiolateral graphs annotated with relationships 604), as well as computational data of estimated induced currents 606 in the voxel space that are registered between subjects. Inputs (element 610) for datafication (element 300) and the forward model 608 include, but are not limited to, EEG, spikes, LFPs, tCS, and iCS data.

For personalized optimization of a stimulation montage to facilitate memory enhancement, the signature template of currents is warped to the particular brain structure. The optimization algorithm/tool (element 310) then operates on the individualized template of the desired currents (i.e., forward model 608) to estimate a compatible stimulation montage (i.e., neural stimulation patterns that will have desired effect 612), which specifies the scalp locations for the electrodes and stimulation current parameters (e.g., amplitude, frequency) at each electrode. The constraints for optimization are the maximum number of electrodes, maximum current per electrode, and maximum cumulative current from all electrodes. In summary, the system according to embodiments of the present disclosure builds a knowledge representation (element 304) from a set of data (element 614) and behavior (element 602), identifies which currents are most responsible for desired behavioral effect (element 608), and then deduces which neural stimulation patterns will produce that effect (element 612).

In one embodiment, an iterative optimization algorithm is used. In each iteration step, first, SOC search is used to improve the placement of electrodes and, second, gradient descent (see Literature Reference No. 24 for a description of gradient descent) is used to improve the parameters for a given placement. For electrode placement, a finite set of possible stimulation sites is used (e.g., 256 predefined locations on a head cap), and the goal is to find the optimal pattern of electrodes from these locations. SOC search uses a self-organized critical (SOC) process (see Literature Reference No. 3) to generate search patterns. As shown in FIG. 10, the SOC process can be defined on an arbitrary graph 1000. In each iteration step of an optimization (i.e. sample sequence of avalanches 1002), each avalanche (e.g., element 1004) is mapped in the graph of the SOC process one-to-one onto the graph over which the optimization problem is defined (element 1006).

FIG. 10 illustrates the operation of SOC search to find the ground state of an Ising spin glass. An Ising spin glass is an array of spins 1000 (e.g., electrons with an electromagnetic moment, up or down) and couplings between the spins so that the energy of a spin depends on the orientations (up or down) of the surrounding spins. The ground state is an arrangement of spin orientations so that the total energy of all spins is at a minimum. To find the minimum, SOC search iterates patterns obtained from an SOC process (e.g., the sequence of avalanches 1002 in the Bak-Tang-Wiesenfeld model (Reference No. 3)). Here, each avalanche 1004 is mapped onto the spin array 1006 and marks the spins to be flipped to test if a lower energy state can be obtained. If this change results in a lower energy, the resulting spin arrangement forms the new baseline for optimization, otherwise the new spin arrangement is discarded. This process repeats until a desired optimum is reached. Refer to Reference No. 21 for additional details.

Because of the high-dimensionality ($N \sim 10^5$) of the electrode-placement problem, the optimization is solved with SOC search, which iteratively finds and refines the locations of the electrodes that should be active. The idea is to approximate the solution with coarser resolutions, initially, then iteratively use the estimated solution to locally increase the resolution (adding columns in the A matrix). This approach significantly increases the accuracy of the solution (reduce the residual), and goes beyond the capabilities of the state-of-the-art inverse models for non-invasive stimulation in being able to deal with spatially distributed current fields in the brain.

Figure 7:
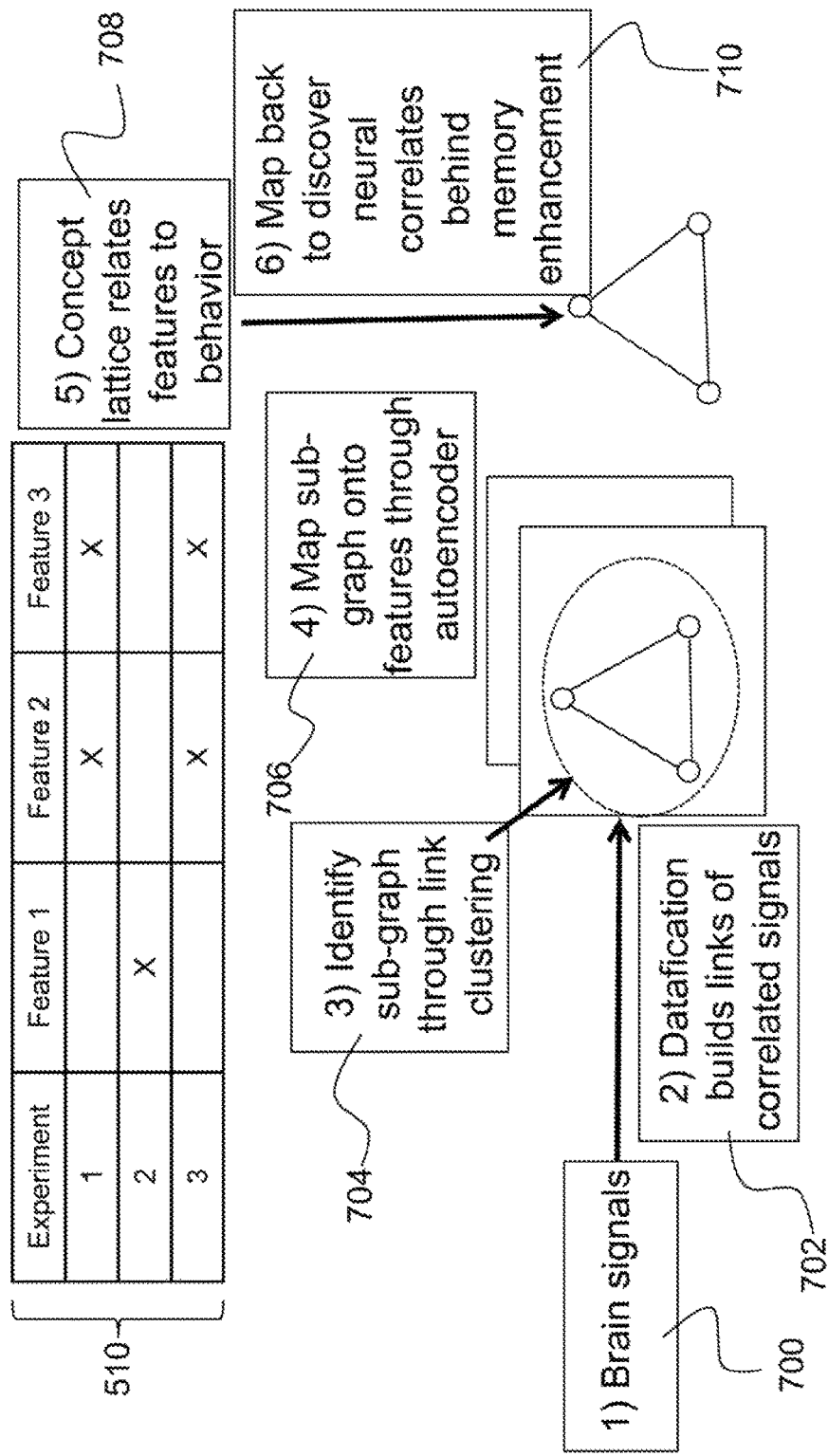
FIG. 7 is an illustration of relating neuroscience data features to behavior to find the neural correlates behind memory enhancement according to embodiments of the present disclosure.

FIG. 7 illustrates how knowledge representation, ultimately a concept lattice derived by steps 1-4 (described below), relates neuroscience data concept features (element 510) to behavior, and can be applied to find the neural correlates behind memory enhancement. If the experiments involve different neural stimulation protocols, the system may be used to optimize the protocol to produce the best behavioral result. Brain signals (step 1, element 700) are processed by the datafication module which builds links of correlated brain signals (step 2, element 702). A sub-graph is identified through link clustering (step 3, element 704), and the sub-graph is mapped onto concept features (element 510) through the autoencoder (step 4, element 706). The concept lattice relates features to behavior (step 5, element 708), and the system maps back to discover neural correlates behind memory enhancement (step 6, element 710). FIG. 8 illustrates a signal graph 800. The adjacency matrix of the graph representation can capture intra-model and cross-model links. For example, intramodel links are correlations between EEG channels (element 506), and cross-models links are correlations between EEG and LFPs (element 610). The whole adjacency matrix is an example of a statistical layer 404 in the knowledge graph 402.

Figure 11:
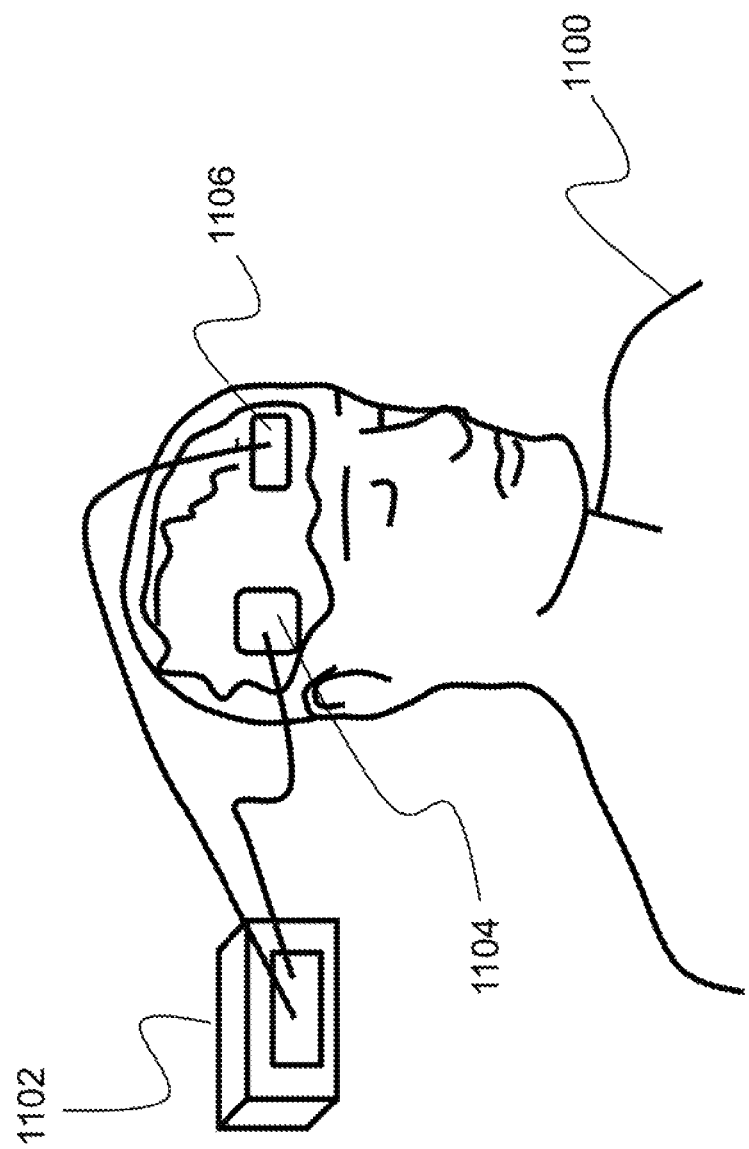
FIG. 11 is an illustration of a subject receiving monitoring and stimulating via electrodes according to embodiments of the present disclosure.

In summary, as illustrated in FIG. 11, the invention described herein is a method and system to affect a desired behavioral result by sensing and intelligently stimulating the brain of a subject 1100 (or group of subjects), encompassing a brain monitoring subsystem 1102 incorporating a set of monitoring electrodes 1104 that can sense brain state (element 314) either invasively (i.e., chronically implanted electrodes providing neural unit or LFP data), or non-invasively (i.e., via EEG). A large number of monitoring electrodes 1104 will give a high resolution result. The system additionally includes a brain stimulation subsystem 1104 (shown as incorporated with the brain monitoring subsystem) incorporating a set of stimulating electrodes 1106 that can apply electrical current stimulation either invasively (i.e., chronically implanted electrodes) or non-invasively (i.e., transcranial current stimulation). As can be appreciated by one skilled in the art, the brain monitoring and brain stimulation subsystems 1104 may also be components of separate devices. Additionally, while a plurality of monitoring electrodes and stimulating electrodes are used in the invention described herein, only one of each type is shown in FIG. 11 for illustrative purposes. In one embodiment, the monitoring electrodes and the stimulating electrodes are co-located.

Further, a forward model predicts behavioral outcomes (element 904) for different stimulations, and a search method (FIG. 10) is used to identify the ideal stimulation pattern related to a desired behavioral outcome. The forward model consists of the following: a graphical representation 402 whose nodes (e.g., elements 410 and 412) describe the data, and edges describe relationships between data items. These relations are topological (element 408), statistical (element 406), and causal (element 404) (see FIG. 4). The data of the graphical representation 402 may include a stimulation montage 316 applied to the brain (if any), either non-invasively or via chronically implanted electrode. Additionally, the data may include EEG data recorded from the monitoring electrodes as a result of a stimulation montage 316 applied via the stimulating electrodes.

The data graph/graphical representation 402 is processed in a series of steps that include one or more of the following. Statistical relationships (element 406) between graph nodes are computed using a wavelet transform, and causality (element 404) is quantified with transfer entropy (TE) and associated transfer entropy (ATE), which transforms continuous time values into a symbolic time series. Spurious indirect links are removed using the correlation matrix technique described in Literature Reference No. 4. Measured and induced data for the non-invasive modality is transformed through a forward model (element 608) into the resulting currents (element 606) in voxels of brain volume, and those currents (element 606) are integrated into the graph representation 402. Data from multiple trials and/or multiple subjects is registered by warping.

Dimensionality reduction is performed on the noisy EEG data across subjects using Support Vector Machine (SVM) (element 900) and Sparse Canonical Correlation Analysis (SCCA) (element 302 and FIG. 9), to select the most salient voxels. Local regions of the graphical representation 402 are compressed with autoencoders 508 and turned into concepts 510 in a concept lattice 512. This concept lattice 512 is formed from a table whose rows are different experiments (i.e., different electrical stimulation montages), and whose columns are a set of concepts (the patterns produced by each local region autoencoder), and the behavioral result.

An inverse mapping technique is used to find a set of stimulus electrode placements and parameters that can recreate the desired brain state (element 314). In an embodiment, the inverse mapping technique is a self-organized criticality form of search (SOC search) (FIG. 10). The stimulating electrode placements and parameters found are applied to the brain via the brain stimulation subsystem, and the behavioral result is monitored. If the result is unsatisfactory, the brain monitoring subsystem is used to update the graph and create a new row in the concept lattice table, and the processes above are repeated. A result is determined to be satisfactory if it fails to achieve the desired behavioral effect. Depending on the desired effect, the determination of success may be subjective, or there may be a task-performance metric. For example, if the goal is to weaken selected memories that are causing post-traumatic stress disorder, the treatment is successful when the subject gets relief. If the goal is to improve certain memories, the ability to recall those memories after a certain amount of time may be the metric for success.

In an embodiment, monitoring and stimulation are done by co-located electrodes. In another embodiment, brain stimulation is accomplished by transcranial magnetic stimulation instead of electrical current. In yet another embodiment of the invention, brain stimulation and/or monitoring is accomplished by chronically implanted electrodes. In another embodiment, behavioral outcomes are promoted for a specific subject, versus a population of subjects.

The invention described herein will have a significant scientific impact by facilitating discoveries related to the neural mechanisms underlying the complicated behavioral and psychological phenomena, and their external control, with either invasive or non-invasive current stimulation. The knowledge representation framework, datafication, and discovery tools will enhance the understanding of the mapping between non-invasive and/or invasive stimulation to neural mechanisms, allowing more fine-tuned stimulation interventions to achieve a behavioral outcome.

The system according to embodiments of the present disclosure will not only advance the understanding of brain function, but it will also provide optimal interventions for behavioral deficits (e.g., memory impairment caused by traumatic brain injury) and psychological disorders (e.g., depression). The invention will significantly enhance the long-term retention of memories in both normal and aging populations, and potentially restore memory function in subjects afflicted with neurodegenerative diseases and brain injuries.

The knowledge representation according to embodiments of the present disclosure can generate more nuanced hypotheses of stimulation-induced currents based on queries for desired behavior. Additionally, discovery tools can then ingest these outputs to better optimize the locations and parameters of stimulation electrodes, with the unique formulation and techniques described herein.

The system according to embodiments of the present disclosure is a process and apparatus for helping human subjects afflicted with behavioral deficits and psychological disorders. As such, it could be part of a service to help wounded soldiers and civilians. Moreover, the invention might be part of a product for memory restoration and enhancement that would have a huge potential commercial market.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for determining a brain stimulation to induce a desired behavior, the system comprising:
   a brain monitoring subsystem comprising a set of monitoring electrodes for sensing brain activity;
   a brain stimulation subsystem comprising a set of stimulating electrodes for applying an electrical current stimulation; and
   one or more processors and a non-transitory computer-readable medium having executable instructions encoded thereon such that when executed, the one or more processors perform operations of:
      registering a set of multi-scale distributed data into a graphical representation, wherein at least a subset of the set of multi-scale distributed data is sensed brain activity, wherein the graphical representation comprises a plurality of nodes, each node representing a data item in the set of multi-scale distributed data, and edges between the plurality of nodes representing relationships between data items, wherein the relationships are at least one of topological, statistical, and causal relationships;
      identifying a sub-graph in the graphical representation;
      mapping the sub-graph onto a set of concept features, generating a concept lattice which relates the set of concept features to a behavioral effect;
      determining an electrical current stimulation to be applied to produce the behavioral effect; and
      causing the electrical current stimulation to be applied via the set of stimulating electrodes.

2. The system as set forth in claim 1, wherein the set of multi-scale distributed data comprises electroencephalogram data recorded from the set of monitoring electrodes as a result of the stimulation montage applied via the set of stimulating electrodes.

3. The system as set forth in claim 1, wherein the one or more processors further perform operations of:
   transforming the set of multi-scale distributed data through a forward simulation into currents in voxels of brain volume; and
   integrating the currents into the graphical representation.

4. The system as set forth in claim 1, wherein the one or more processors further perform an operation of identifying a set of stimulating electrode placements and parameters that can recreate the behavioral effect.

5. The system as set forth in claim 4, wherein the identified set of stimulating electrode placements and parameters are applied via the brain stimulation subsystem, and wherein the brain monitoring subsystem monitors the behavioral effect, wherein if the behavioral effect is unsatisfactory, then the brain monitoring subsystem updates the graphical representation and the one or more processors perform an operation of determining a new electrical current stimulation to be applied to produce a satisfactory behavioral effect.

6. The system as set forth in claim 1, wherein the one or more processors further perform an operation of using self-organized criticality (SOC) to search for electrode locations or settings for brain stimulation.

7. The system as set forth in claim 1, wherein the one or more processors further perform an operation of using a forward simulation to predict behavioral outcomes for various brain stimulations.

8. A computer implemented method for determining a brain stimulation to induce a desired behavior, the method comprising an act of:
   causing one or more processors to execute instructions encoded on a non-transitory computer-readable medium, such that upon execution, the one or more processors perform operations of:
      registering a set of multi-scale distributed data into a graphical representation, wherein at least a subset of the set of multi-scale distributed data is sensed brain activity obtained from a brain monitoring subsystem comprising a set of monitoring electrodes, wherein the graphical representation comprises a plurality of nodes, each node representing a data item in the set of multi-scale distributed data, and edges between the plurality of nodes representing relationships between data items, wherein the relationships are at least one of topological, statistical, and causal relationships;
      identifying a sub-graph in the graphical representation;
      mapping the sub-graph onto a set of concept features, generating a concept lattice which relates the set of concept features to a behavioral effect;
      determining an electrical current stimulation to be applied to produce the behavioral effect via a brain stimulation subsystem comprising a set of stimulating electrodes; and
   causing the electrical current stimulation to be applied via the set of stimulating electrodes.

9. The method as set forth in claim 8, wherein the one or more processors further perform operations of:
   transforming the set of multi-scale distributed data through a forward simulation into currents in voxels of brain volume; and
   integrating the currents into the graphical representation.

10. The method as set forth in claim 8, wherein the one or more processors further perform an operation of identifying a set of stimulating electrode placements and parameters that can recreate the behavioral effect.

11. The method as set forth in claim 10, wherein the identified set of stimulating electrode placements and parameters are applied via the brain stimulation subsystem, and wherein the brain monitoring subsystem monitors the behavioral effect, wherein if the behavioral effect is unsatisfactory, then the brain monitoring subsystem updates the graphical representation and the one or more processors perform an operation of determining a new electrical current stimulation to be applied to produce a satisfactory behavioral effect.

12. The method as set forth in claim 8, wherein the one or more processors further perform an operation of using self-organized criticality (SOC) to search for electrode locations or settings for brain stimulation.

13. The method as set forth in claim 8, wherein the one or more processors further perform an operation of using a forward simulation to predict behavioral outcomes for various brain stimulations.

14. A computer program product for determining a brain stimulation to induce a desired behavior, the computer program product comprising:
   computer-readable instructions stored on a non-transitory computer-readable medium that are executable by a computer having one or more processors for causing the processor to perform operations of:
      registering a set of multi-scale distributed data into a graphical representation, wherein at least a subset of the set of multi-scale distributed data is sensed brain activity obtained from a brain monitoring subsystem comprising a set of monitoring electrodes, wherein the graphical representation comprises a plurality of nodes, each node representing a data item in the set of multi-scale distributed data, and edges between the plurality of nodes representing relationships between data items, wherein the relationships are at least one of topological, statistical, and causal relationships;
      identifying a sub-graph in the graphical representation;
      mapping the sub-graph onto a set of concept features, generating a concept lattice which relates the set of concept features to a behavioral effect;
      determining an electrical current stimulation to be applied to produce the behavioral effect via a brain stimulation subsystem comprising a set of stimulating electrodes; and
   causing the electrical current stimulation to be applied via the set of stimulating electrodes.

15. The computer program product as set forth in claim 14, further comprising instructions for causing the one or more processors to perform operations of:
   transforming the set of multi-scale distributed data through a forward simulation into currents in voxels of brain volume; and
   integrating the currents into the graphical representation.

16. The computer program product as set forth in claim 14, further comprising instructions for causing the one or more processors to further perform an operation of identifying a set of stimulating electrode placements and parameters that can recreate the behavioral effect.

17. The computer program product as set forth in claim 16, wherein the identified set of stimulating electrode placements and parameters are applied via the brain stimulation subsystem, and wherein the brain monitoring subsystem monitors the behavioral effect, wherein if the behavioral effect is unsatisfactory, then the brain monitoring subsystem updates the graphical representation and the one or more processors perform an operation of determining a new electrical current stimulation to be applied to produce a satisfactory behavioral effect.

18. The computer program product as set forth in claim 14, further comprising instructions for causing the one or more processors to further perform an operation of using self-organized criticality (SOC) to search for electrode locations or settings for brain stimulation.

19. The computer program product as set forth in claim 14, further comprising instructions for causing the one or more processors to further perform an operation of using a forward simulation to predict behavioral outcomes for various brain stimulations.

* * * * *